United States Patent [19]
Hsieh et al.

[11] Patent Number: 6,038,278
[45] Date of Patent: Mar. 14, 2000

[54] METHOD AND APPARATUS FOR HELICAL MULTI-FRAME IMAGE RECONSTRUCTION IN A COMPUTED TOMOGRAPHY FLUORO SYSTEM

[76] Inventors: Jiang Hsieh, 19970 W. Keswick Ct.; Kishore Acharya, 1325 Ridgeway Rd., both of Brookfield, Wis. 53045; Sandeep Dutta, 3150 S. Pinewood Creek Y107, New Berlin, Wis. 53151

[21] Appl. No.: 09/108,676

[22] Filed: Jul. 1, 1998

[51] Int. Cl.[7] .................................................. H61B 6/03
[52] U.S. Cl. .................................. 378/15; 378/4; 378/961
[58] Field of Search ................................. 378/4, 15, 901; 382/131

[56] References Cited

U.S. PATENT DOCUMENTS

| | | | |
|---|---|---|---|
| 4,736,399 | 4/1988 | Okazaki | 378/98.2 |
| 5,412,563 | 5/1995 | Cline et al. | 345/420 |

*Primary Examiner*—David Vernon Bruce
*Attorney, Agent, or Firm*—John S. Beulick; Christian G. Cabou; Phyllis Y. Price

[57] ABSTRACT

The present invention, in one form, is a system for performing image reconstruction from projection data acquired in a helical scan. More specifically, the system implements an incremental reconstruction algorithm for helical scan projection data which does not require filtering, weighting and backprojecting such projection data for generating each image. Particularly, a segmentation algorithm divides the projection into a plurality of segments so that subsequent images are generated by generating image data only for those segments that have changed from the base image.

34 Claims, 2 Drawing Sheets

METHOD AND APPARATUS FOR HELICAL MULTI-FRAME IMAGE RECONSTRUCTION IN A COMPUTED TOMOGRAPHY FLUORO SYSTEM

FIELD OF THE INVENTION

This invention relates generally to computed tomography (CT) imaging and more particularly, to multi-frame image reconstruction in a CT fluoroscopic system.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce an attenuation profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Certain reconstruction process steps are known to produce noise structures in an image. For example, and during a "cine" scan, i.e., a scan in which the patient remains stationary while the data for the prescribed number of slices is acquired, underscan weighting ("USW") is employed to reduce motion artifacts that result when patient anatomy moves during the scan. Underscan weighting algorithms typically weight the collected data as a function of view angle and detector channel index. Specifically, prior to filtered back projection, the data is weighted according to a underscan weighting factor, which is a function of both the view angle and detector angle. Particularly, projection data is first filtered, then weighted, and subsequently back-projected to generate each image.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighting ("HW") algorithms which weight the collected data as a function of view angle and detector channel index. Specifically, prior to filtered back projection, the data is weighted according to a helical weighting factor, which is a function of both the view angle and detector angle. As with underscan weighting, in a HW algorithm, projection data is filtered, weighted, and backprojected to generate each image.

In a cine scan context and a helical scan context, the same projection data is repeatedly filtered, weighted, and back-projected even though it is continually assigned the same weight. For example, projection data $P_1$ may be weighted $w_1$ to generate a first image $I_1$, and also weighted $w_2$ to generate a second image $I_2$. However, second image $I_2$ cannot be generated without re-filtering, re-weighting and re-backprojecting projection data $P_1$. The underscan weighting algorithms and the helical weighting algorithms both require each image $I_1$ and $I_2$ to be independently generated from projection data $P_1$. Therefore, significant computational redundancy occurs with both helical weighting algorithms and underscan weighting algorithms.

Reconstruction techniques for improving certain aspects of image generation are known. For example, overscan weighting is employed to decrease computational redundancy associated with reconstructing overlapping images with projection data. Particularly, in overscan weighting, the collected projection data is weighted only as a function of view angle. Therefore, while not completely eliminating computational redundancy, overscan weighting reduces the computations necessary for image reconstruction. Moreover, overscan weighting is known to reduce motion artifacts that result when patient anatomy moves during a 360 degree CT scan. Patient motion causes views at the beginning and ending projections to be inconsistent and discontinuous. However, while overscan weighting is successful in reducing some motion artifacts, overscan weighting is not as effective as, for example, other helical weighting algorithms. Therefore, the overscan weighting is often precluded during helical scans.

In CT fluoroscopic systems ("CT Fluoro"), it is known to generate sequential frames of images. A frame, like a view, corresponds to a two dimensional slice taken through the imaged object. Particularly, projection data is processed to construct an image frame of the object. Typically, projection data is not weighted so that the frame rate may be increased. However, non-weighted projection data is known to produce noticeable shading and streaking in generated images. To reduce such shading and streaking, helical weighting algorithms may be used to weight the projection data corresponding to each frame. However, the more often projection data is filtered, weighted and backprojected, the slower the frame rate. The frame rate is thus limited to the computational capabilities of the CT Fluoro system.

It would be desirable, of course, to decrease computational redundancy in helical scan image reconstruction. It also would be desirable to facilitate altering the number of views per frame and offer reasonable trade-offs between views per frame and frame rate in CT fluoroscopic helical image reconstruction.

SUMMARY OF THE INVENTION

These and other objects may be attained in a system which, in one embodiment, implements a segmentation algorithm for dividing the helical scan projection data into a plurality of segments so that the image data contained in unchanged segments does not require re-filtering, weighting and backprojecting for generation of each subsequent image.

Particularly, and in accordance with one embodiment of the present invention, the segmentation algorithm divides the projection data into segments which contribute to one segment image data. A weighting algorithm is then applied to the segment projection data to generate weighted image data and unity weight image data.

Subsequent images are generated from the base image projection data. Specifically, image data from unchanged segments may be utilized from the base image data to generate the subsequent image without filtering, weighting and backprojecting.

In order to improve computational efficiency, the number of segments may be altered to select from a number of views per segment. Specifically, a DAS sampling rate may be adjusted to alter the number of views per segment. Alternatively, the number of views per segments may be altered.

Using the incremental reconstruction algorithm described above enables reconstruction of subsequent images from helical scan data without requiring that each image be independently generated. Further, the computational costs and expenses of generating images in CT Fluoro helical image reconstruction are reduced. Such algorithm also decreases the processing time and offers reasonable trade-offs between number of views and frame rate. In addition, the present image algorithm is not believed to significantly decrease image quality.

DETAILED DESCRIPTION OF THE DRAWINGS

Figure 1:
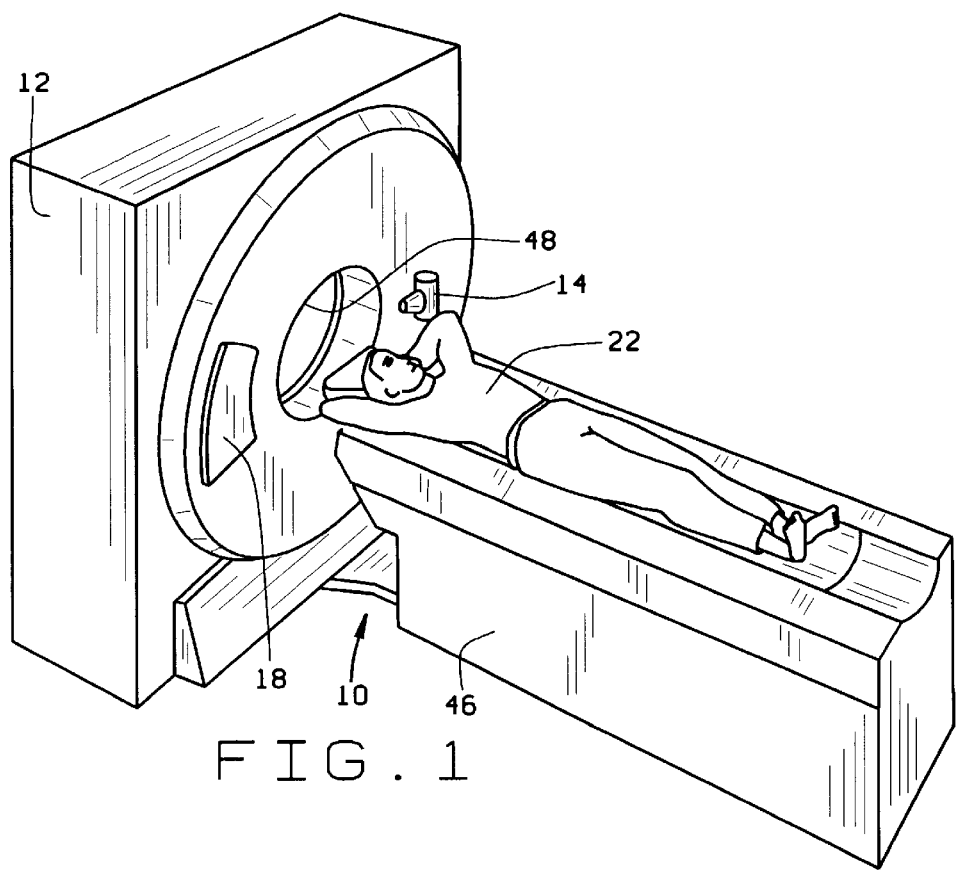
FIG. 1 is a pictorial view of a CT imaging system.
Figure 2:
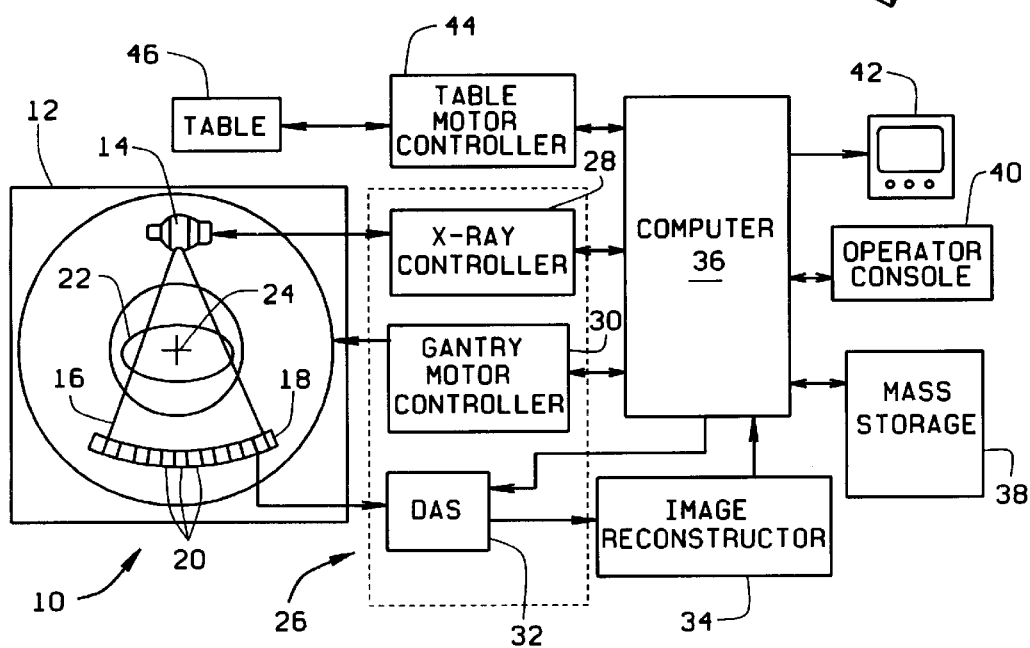
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The known helical reconstruction algorithms may generally be classified as Helical Extrapolative (HE) or Helical Interpolative (HI) algorithms. These algorithms typically apply a weighting factor to the projection data in order to reconstruct an image. This weighting factor is generally based on, i.e., dependent upon, both the fan angle and view angle. While the HE and HI algorithms provides generally acceptable image quality, such algorithms employ significant computational redundancies, and require significant hardware costs when reconstruction speed is crucial. For example, almost all projections that are used to generate an original image will have to be re-weighted, re-filtered, and re-backprojected to generate a new image that is even a small fraction of the rotation apart. Particularly, even where a significant amount of overlap occurs in projections of sequential images, to generate n images per gantry rotation, n times the amount of computation that is needed to generate a single image is needed during the gantry rotation.

The following discussion of a segmentation algorithm sometimes refers specifically to CT Fluoro systems using a helical scan or a cine scan. The segmentation algorithm, however, is not limited to practice in connection with such systems, and may be used with other CT systems. Further, in one embodiment, the segmentation algorithm would be implemented in computer 36 and would process, for example, data stored in mass storage 38. Many other alternative implementations are, of course, possible.

In accordance with one embodiment of the present invention, projection data to be used to generate base image data for a base image is divided into a plurality of segments. Specifically, to generate the base image, gantry 12 rotates one full revolution plus a view angle of $\beta_0$, i.e., over the range $(0, 2\pi + \beta_0)$, to acquire projection data. Angle $\beta_0$ represents the angle of gantry rotation in excess of 360° during a helical scan. Views, V, represent the number of views collected per $2\pi$ gantry rotation, and views $V_L$ is the number of views contained in $(0 \leq \beta \leq \beta_0)$ view angle. The segmentation algorithm divides the projection data into M segments for every $2\pi$ angular span. For example, where system 10 speed is one second per gantry rotation and a data acquisition period of DAS 32 is five seconds, the projection data is divided into 5M segments. More specifically, the segmentation algorithm generates subsequent images from changed segments and allows selection of segment quantity and size from a variety of values, including segments having a different number of views from adjacent segments. Segment quantity and size are selected so that the number of views contained in the $k^{th}$ segment is identical to the $(k+M)^{th}$ segment and the quantity of views contained in any segment is greater than or equal to the number of views in $V_L$.

After dividing the projection data into segments and filtering the data, an overscan weighting algorithm is applied to the filtered projection data of each segment to generate overscan weight image data and unity image data for each segment. Specifically, the overscan weighting algorithm applies a weighting factor $w(\beta)$ to the projection data of each segment acquired at different view angles $\beta$ to generate an overscan weight image, $O_k$, for each segment. Note that for weighting purposes the starting view angle, β, for each segment is set to zero. A unity weighting factor is then applied to the projection data of each segment to generate a unity weight image, $U_k$, for each segment. Particularly, the filtered projection data is multiplied by the generated weighting factor, and then backprojected.

Utilizing segment image data from the base image data, subsequent image data is generated. More specifically and in one embodiment, the angular span for segment k is $\beta_k$ and the weights corresponding to regions $(0 \leq \beta \leq \beta_0)$ and $(2\pi \leq \beta \leq 2\pi + \beta_0)$ are complimentary to one another. Particularly, a view angle, $\beta_k$, for a first projection of a subsequent image is selected. Projection data contributing to the subsequent image is in the range $(\beta_k, 2\pi + \beta_k + \beta_0)$. By executing the segmentation algorithm, an updated weighting factor based on each view angle, $\beta_k$, and an overscan weighting factor w(β) within the range $(0, 2\pi + \beta_0)$ is generated. Specifically, segmentation algorithm determines an updated weighting factor to apply to previously filtered, weighted, and backprojected base image projection data so that the subsequent image is generated without re-filtering, re-weighting and re-backprojecting all of the base image projection data.

Figure 3:
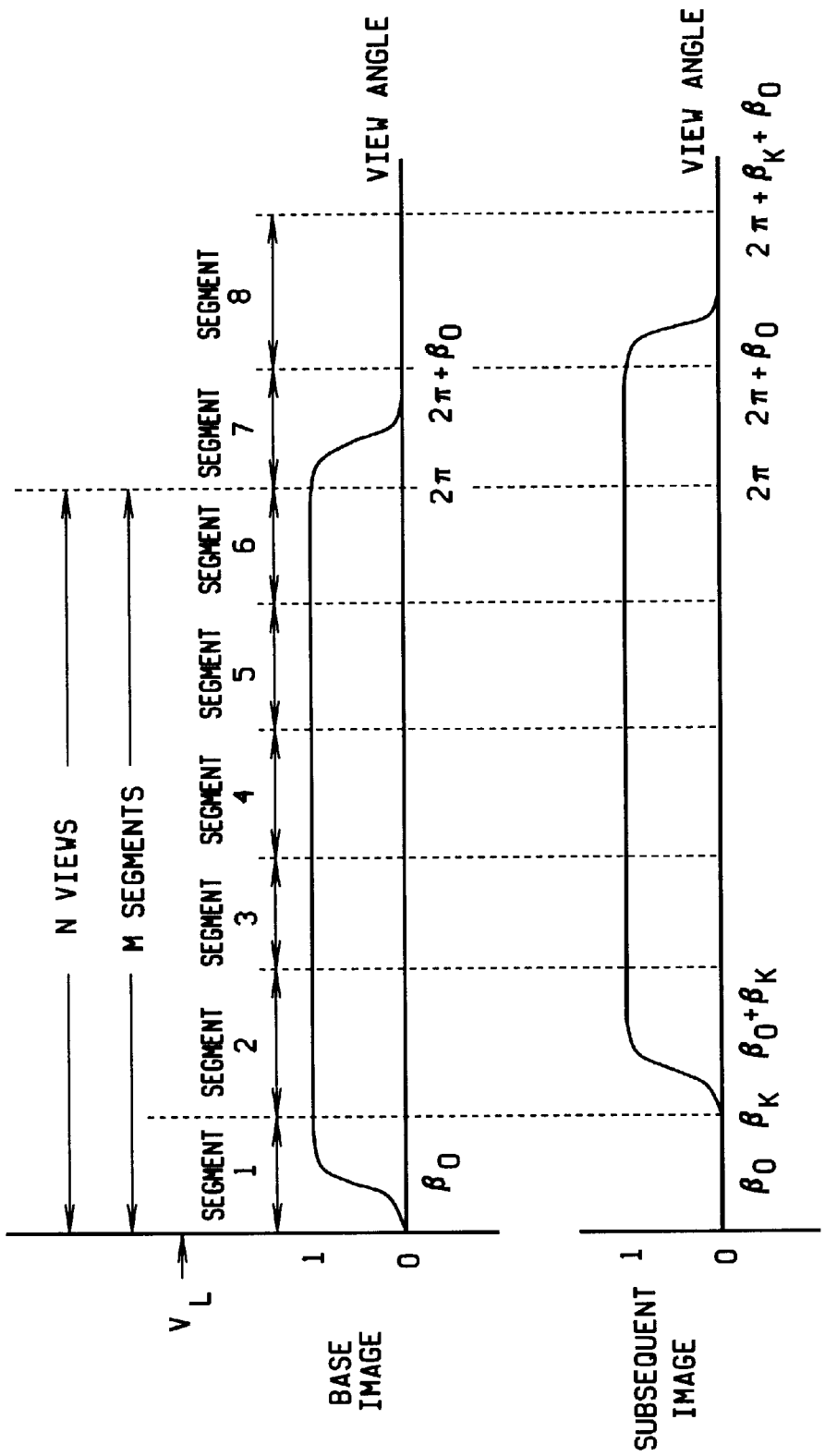
FIG. 3 is a graph illustrating overscan weighting factors versus view angle for generating a subsequent image from a base image in accordance with one embodiment of the present invention.

FIG. 3 (top) for example, is a graph illustrating overscan weighting factors versus view angle for generating a first image in accordance with one embodiment of the present invention. FIG. 3 (bottom) is a graph illustrating overscan weighting factors versus view angle for generating a subsequent image, wherein the subsequent image begins at view angle $\beta_k$. Particularly, $\beta_k$ represents the view angle at which the first projection of the subsequent image is located, and the curve illustrates the weights applied to projection data for the generation of the subsequent image.

As shown in FIG. 3, the weighting factor for a majority of the segments remain unchanged between the base image and the k$^{th}$ subsequent image. For example and as shown in FIG. 3, the weighting factors of segments 3 through 6 are unchanged between the base image and the k$^{th}$ image. As a result, the k$^{th}$ image is:

$$P_k = O_k - O_{k+M} + \sum_{i=k+1}^{k+M} U_i$$

where:

$O_k$ is overscan weighted image data for segment k;
$U_i$ is unity weighted image data for segment i; and
$k \geq 1$.

In addition, where M>6 and k>1, the k$^{th}$ image is:

$$P_k = P_{k-1} - O_{k-1} - U_k + O_k + O_{k+M-1} + U_{k+M} - O_{k+M}$$

where:

$O_k$ is overscan weighted image data for segment k;
$U_k$ is unity weighted image data for segment k;
k>1; and
M>6.

Therefore, the previously filtered, weighted and back-projected base image projection data is simply re-used to generate the subsequent image. Conversely, the overscan weighting factors applied to projection data in the segments 1 and 2, $(0, \beta_k + \beta_0)$, and segments 7 and 8, $(2\pi, 2\pi + \beta_k + \beta_0)$, differ between the first image and the subsequent image. The weighting algorithm thus generates weighting factors and image data within these ranges. More particularly, the weighting algorithm generates updated weighting factors which, when applied to the base image data, re-weights the base image data in the changed segments so that the base data contribution to the subsequent image is in accordance with the overscan weighting factors illustrated in FIG. 3b. However, such base image data is not re-filtered. Therefore, a substantial portion of the subsequent image is generated without re-filtering, re-weighting, or re-backprojecting the previously acquired base image data. Accordingly, significant amounts of filtering, multiplication, and back projection are eliminated, thus improving the computational efficiency of the system. More specifically, the only projection data required to be filtered to generate the subsequent image is projection data of segments previously not filtered for generating the base image data. As described above, this is not a substantial amount of data.

In one embodiment, the number of segments, M, is selected so that each segment contains an identical number of views, $v_k$. However, such a selection may be impractical. For example, the number of views contained in one gantry rotation, N, may not be divisible by the number of segments M. In addition, system 10 may include multiple processors, or processing pipes, D, used in parallel for image reconstruction, however, the number of views contained in each segment may not be divisible by the number of processors.

In another embodiment, a sampling rate of DAS 32 is adjusted so that the number of views after compression per $2\pi$ rotation, v, divided by the quantity of processor pipes D times the number of segment results in a whole

TABLE 1

| image frame rate/s | DAS trigger rate/s | number of compressed views/s | number of views per segment | number of views per processor | % change in DAS rate from 984 |
|---|---|---|---|---|---|
| 8 | 960 | 640 | 80 | 10 | -2.4% |
| 7 | 1008 | 672 | 96 | 12 | +2.4% |
| 7 | 924 | 616 | 88 | 11 | +6.1% |
| 6 | 1008 | 672 | 112 | 14 | +2.4% |
| 6 | 936 | 624 | 104 | 13 | -4.9% |

TABLE 2

| image frame rate | number of views in segment | | | | | | | | | | | | | | | | | comments |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | |
| 8 | 88 | 80 | 80 | 80 | 88 | 80 | 80 | 80 | 88 | 80 | 80 | 80 | 88 | 80 | 80 | 80 | 88 | 88 on 4th |
| 7 | 80 | 96 | 96 | 96 | 96 | 96 | 96 | 80 | 96 | 96 | 96 | 96 | 96 | 96 | 80 | 96 | 96 | 80 on 7th |
| 6 | 104 | 112 | 112 | 104 | 112 | 112 | 104 | 112 | 112 | 104 | 112 | 112 | 104 | 112 | 112 | 104 | 112 | 104 on 3rd | integer. As shown in Table 1, illustrating an exemplary embodiment where DAS sampling rate is normally 984 views per rotation, the sampling rate of DAS 32 may be adjusted so that the selected number of views per segment are collected for a given image frame rate.

In an alternative embodiment, each segment includes multiple views and may be of a non-uniform size (different size from the neighboring segments). Specifically, the size of each segment may be altered so that the number of views in each segment divided by the number of pipes D is a whole number and the total number of views contained in the M segments is equal to the number of views per $2\pi$ rotation of gantry 12. In addition the segments must conform to the restrictions that the number of views contained in the $k^{th}$ segment is identical to the $(k+M)^{th}$ segment and the number of views in any segment must be greater than or equal to the $V_L$. An exemplary example is shown in Table 2.

In another embodiment, system 10 includes a convolution algorithm that simultaneously generates multiple views of a image data. Specifically, a complex FFT convolution algorithm simultaneously generates two views from the image data. More specifically, one view of N elements will be treated as the real part and the second view of N elements will be treated as the imaginary part of a complex sequence of length N. Particularly, a sequence y(n) is formed, sequence y(n) is:

$$y(n)=v_i(n)+jv_m(n)$$

where:

n is the number of sample points and n=0, 1, 2, ..., N−1;
i is the view number and i=0, 1, 2, ..., $N_{v-1}$;
m is the view number and i=0, 1, 2, ..., $N_{v-1}$;
$v_i$ corresponds to the $i^{th}$ zero padded view; and
$v_m$ corresponds to the $m^{th}$ zero padded view. $v_i$ and $v_m$ may be from the same view, different views or different volumetric computed tomography slices.

After forming sequence y(n), a complex FFT of y(n), Y(n), is generated. An extended frequency domain response of the convolution kernel to N points is then generated where the response is:

$$H(k)=H(N-k)$$

where k=N/2, ..., N−1; and

H(k) is the real FFT of the kernel h(n), which is an even function. Utilizing the extended frequency domain response H(k), Z(k) is computed:

$$Z(k)=Y(k).H(k).$$

An inverse complex FFT of Z(k), z(n) is generated and the result is separated, or isolated into Real z(n) and Imaginary z(n) portions or parts. Specifically, the portions are:

$C_{vi}$=Real z(n);
$C_{vm}$=Imaginary z(n), where:

$C_{vi}$ is the convolved $i^{th}$ view; and
$C_{vm}$ is the $m^{th}$ view.

Utilizing the convolution algorithm reduces the numbers of forward and reverse complex FFT operations that must be performed. For example, where four views are processed, known convolution algorithms must perform four forward and four inverse Real FFT operations. However, the convolution algorithm described generates the image data by requiring only two forward and two inverse complex FFT operations. As a result, the computational efficiency is improved and the amount of time required to generate the images may be reduced.

The above described algorithm facilitates improving computational efficiency without degrading image quality in CT Fluoro image reconstruction. Such algorithm also decreases the processing time and offers reasonable trade-offs between number of views and frame rate.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a CT Fluoro system. Many other CT systems may be used. Similarly, while the values of $\beta$ and $\beta_k$ are described herein as being selected as the final stage of image quality evaluation, any or all of these values may be pre-selected and stored in the computer. Furthermore, the overscan weights described are determined in accordance to a non-linear function, i.e., $w(\beta)$ is not proportional to $\beta$. However, the overscan weights may be generated with a linear function, or with a different non-linear function. In addition, while the invention is described in connection with a helical scan, the invention may also be used in connection with a cine scan. Accordingly, the spirit and scope of the invention are to be limited only by the terms of the appended claims.

What is claimed is:

1. A system for producing a base tomographic image and a subsequent tomographic image of an object using projection data acquired in a scan, said system comprising an x-ray source and a detector array, said detector array comprising a plurality of detectors, said system configured to:

apply a segmentation algorithm to the projection data to generate base image data comprising a plurality of segments;

generate image data for each segment; and generate subsequent image data based on said image data of each segment.

2. A system in accordance with claim 1 wherein to generate said image data for each segment, said system is configured to generate overscan weighted image data and unity weighted image data for each segment.

3. A system in accordance with claim 2 wherein to generate said base image data, said system is configured to divide the base image data into M segments for every $2\pi$ angular span.

4. A system in accordance with claim 3 wherein said subsequent image data P of segment k is:

$$P_k = O_k - O_{k+M} + \sum_{i=k+1}^{k+M} U_i$$

where:

$O_k$ is overscan weighted image data for segment k;
$U_i$ is unity weighted image data for segment i; and
$k \geq 1$.

5. A system in accordance with claim 3 wherein said subsequent image data P of segment k is:

$$P_k = P_{k-1} - O_{k-1} - U_k + O_k + O_{k+M-1} + U_{k+M} - O_{k+M}$$

where:

$O_k$ is overscan weighted image data for segment k;
$U_k$ is unity weighted image data for segment k;
k>1; and
M>6.

6. A system in accordance with claim 3 wherein each segment comprises multiple number of views.

7. A system in accordance with claim 6 wherein the number of views in $k^{th}$ segment equals the number of views in $(k+M)^{th}$ segment.

8. A system in accordance with claim 7 further comprising a number of processor pipes D and wherein the number of views in each segment is greater than or equal to the number of views in $0 \leq \beta \leq \beta_0$,
where:
$\beta$ is a view angle; and
$\beta_0$ is an angle of gantry rotation in excess of 360° for image reconstruction.

9. A system in accordance with claim 8 further comprising a data acquisition system (DAS) and wherein to select the number of views per segment, said system is configured to adjust a DAS data sampling rate so that the selected number of views per segment are collected.

10. A system in accordance with claim 9 wherein said adjusted sampling rate is:

$$R=V/(D*M),$$

where:
R is a whole integer number; and
V is a number of views per $2\pi$ rotation of gantry.

11. A system in accordance with claim 8 wherein the selected number of views in each processor pipe is:

$$V_k=(\text{number of views in segment k})/D$$

where:
$v_k$ is a whole integer.

12. A system in accordance with claim 2 further comprising a convolution algorithm to simultaneously generate two views of image data.

13. A system in accordance with claim 12 wherein said convolution algorithm is configured to:
form a sequence y(n);
determine Y(k); and
determine an extended frequency domain response to N−1 points,
where:
$y(n)=v_i(n)+jv_m(n)$;
Y(k) is a complex FFT of y(n);
n is a number of sample points ranging from 0 to N−1;
i is a view number ranging from 0 to $N_{v-1}$;
m is a view number ranging from 0 to $N_{v-1}$;
$v_i$ corresponds to the $i^{th}$ zero padded view; and
$v_m$ corresponds to the $m^{th}$ zero padded view.

14. A system in accordance with claim 13 wherein i is not equal to m.

15. A system in accordance with claim 13 wherein $v_i$ and $v_m$ correspond to different slices of a volumetric scan.

16. A system in accordance with claim 13 wherein said extended frequency domain response is:

$$H(k)=H(N-k),$$

where:

k=N/2 . . . N−1; and
spatial response of a h(n) kernel is an even function.

17. A system in accordance with claim 13 wherein said convolution algorithm is further configured to:
determine a Z(k);
determine a inverse complex FFT, z(k), of Z(k); and
isolate real part $Cv_i$ and imaginary part $Cv_m$ of z(n),
where:

$$Z(k)=Y(k).H(k).$$

18. A method for reconstructing an image of an object in a computed tomography (CT) system using projection data acquired in a scan, the CT system comprising an x-ray source and a detector array, said detector array comprising a plurality of detectors, said method comprising the steps of:
applying a segmentation algorithm to the projection data to generate base image data comprising a plurality of segments;
generating image data for each segment; and
generating subsequent image data based on the image data of each segment.

19. A method in accordance with claim 18 wherein generating the image data for each segment comprises the step of generating overscan weighted image data and unity weighted image data for each segment.

20. A method in accordance with claim 19 wherein generating the base image data comprises the step of dividing the base image data into M segments for every $2\pi$ angular span.

21. A method in accordance with claim 20 wherein the subsequent image data P of segment k is:

$$P_k = O_k - O_{k+M} + \sum_{i=k+1}^{k+M} U_i,$$

where:
$O_k$ is overscan weighted image data for segment k;
$U_i$ is unity weighted image data for segment i; and
$k \geq 1$.

22. A method in accordance with claim 20 wherein the subsequent image data P of segment k is:

$$Pk=Pk-1-Ok-1-Uk+Ok+Ok+M-1+Uk+M-Ok+M,$$

where:
$O_k$ is overscan weighted image data for segment k;
$U_k$ is unity weighted image data for segment k;
k>1; and
M>6.

23. A method in accordance with claim 20 wherein each segment comprises multiple number of views.

24. A method in accordance with claim 20 wherein the number of views in $k^{th}$ segment equals the number of views in $(k+M)^{th}$ segment.

25. A method in accordance with claim 23 herein the CT system further comprises a number of processor pipes D and wherein the number of views in each segment is greater than or equal to the number of views in $0 \leq \beta \leq \beta_0$,
where:
$\beta$ is a view angle; and
$\beta_0$ is an angle of gantry rotation in excess of 360° for image reconstruction.

26. A method in accordance with claim 25 wherein the CT system further comprises a data acquisition system (DAS)

and wherein selecting the number of views per segment comprises the step of adjusting a DAS data sampling rate so that the multiple number of views per segment are collected.

27. A method in accordance with claim 26 wherein said adjusted sampling rate is:

$$R = V/(D*M),$$

where:

R is a whole integer number; and

V is a number of views per $2\pi$ rotation of gantry.

28. A method in accordance with claim 26 wherein the selected number of views in processor pipe is:

$V_k$=(number of views in segment k)/D where:

$V_k$ is a whole integer.

29. A method in accordance with claim 18 further comprising the step of applying a convolution algorithm to simultaneously generate two views of image data.

30. A method in accordance with claim 29 wherein applying the convolution algorithm comprises the steps of:

forming a sequence y(n);

determining Y(k); and determining an extended frequency domain response to N−1 points, where:

$y(n) = v_i(n) + jv_m(n)$;

Y(k) is a complex FFT of y(k);

n is a number of sample points ranging from 0 to N−1;

i is a view number ranging from 0 to $N_{v-1}$;

m is a view number ranging from 0 to $N_{v-1}$;

$v_i$ corresponds to the $i^{th}$ zero padded view; and $v_m$ corresponds to the $m^{th}$ zero padded view.

31. A method in accordance with claim 30 wherein i is not equal to m.

32. A method in accordance with claim 30 wherein generating subsequent image data further comprises the step of generating slice data and wherein $v_i$ and $v_m$ are from different slices.

33. A method in accordance with claim 30 wherein the extended frequency domain response is:

$$H(k) = H(N-k),$$

where:

k=N/2 ... N−1; and spatial response of a h(n) kernel is an even function.

34. A method in accordance with claim 30 wherein applying the convolution algorithm further comprises the steps of:

determining Z(k);

determining an inverse complex FFT, z(k), of Z(k); and isolating real part $Cv_i$ and imaginary part $Cv_m$ of z(n), where:

$$Z(k) = Y(k).H(k).$$

* * * * *

UNITED STATES PATENT AND TRADEMARK OFFICE
CERTIFICATE OF CORRECTION

PATENT NO.    : 6,038,278
DATED         : March 14, 2000
INVENTOR(S)   : Hsieh et al.

It is certified that error appears in the above-identified patent and that said Letters Patent is hereby corrected as shown below:

<u>Title page,</u>
Item [73], insert the following:
-- [73] Assignee: General Electric Company, Schenectady, NY --

Signed and Sealed this

Eighth Day of October, 2002

Attest:

Attesting Officer

JAMES E. ROGAN
*Director of the United States Patent and Trademark Office*